United States Patent [19]

Laties et al.

[11] 4,350,676

[45] Sep. 21, 1982

[54] OPHTHALMIC USE OF CARBOXYFLUORESCEIN

[76] Inventors: Alan M. Laties, 2403 Spruce St., Philadelphia, Pa. 19103; Richard A. Stone, 1720 Sue Ellen Dr., Havertown, Pa. 19083

[21] Appl. No.: 265,934

[22] Filed: May 21, 1981

[51] Int. Cl.$^3$ .................... A61K 49/00; G01N 21/25; G01N 21/64
[52] U.S. Cl. ............................................ 424/7; 424/9
[58] Field of Search ........................................ 424/7, 9

[56] References Cited

U.S. PATENT DOCUMENTS 3,306,820  2/1967  Krezanoski ............................. 424/7

OTHER PUBLICATIONS

Grimes et al., Biol. Abs., vol. 70, Nov. 15, 1980, Ab. No. 68201.
Pitet et al., Chem. Abs., vol. 78, 1973, Ab. No. 70919r.

*Primary Examiner*—Anna P. Fagelson
*Attorney, Agent, or Firm*—Caesar, Rivise, Bernstein & Cohen, Ltd.

[57] ABSTRACT

A method of using carboxyfluorescein in ophthalmic studies comprising applying of the eye an effective amount of at least one active isomer of carboxyfluorescein.

3 Claims, No Drawings

OPHTHALMIC USE OF CARBOXYFLUORESCEIN

This invention relates to the ophthalmic use of carboxyfluorescein. A principal aspect of the present invention involves the use of carboxyfluorescein as an angiographic dye to study the eye in health and disease. However, the present invention contemplates other ophthalmic uses of carboxyfluorescein, such as in topical applications to the eye. The present invention further contemplates the use of carboxyfluorescein in renal physiology and in liver function studies.

The internal structures of the eye are transparent, allowing light to pass unimpeded from the cornea in the front to the light sensitive cells at the back, the outer part, of the retina. In order for light to go through to the light sensitive cells, the retina, for practical purposes, is transparent. The retinal blood vessels are both on the surface and within the retina; they are visible through the front of the eye when properly illuminated. They appear red in color because of their content of blood.

For the retina to obtain a proper supply of nutrients, such nutrients must either pass through the walls of the retinal blood vessels or through or between the walls of cells just outside the retina, called the pigment epithelium. In each case, different substances do or do not pass through. The fact that many substances are held back from passage is denoted by the term "blood-retinal barrier". Thus, it might be said that the structures involved in the blood-retina barrier are the lining cells of blood vessels and a continuous sheet of epithelial cells at the outer surface of the retina. The more general term "blood-ocular barrier" includes the blood-retinal barrier, but also includes blood vessels and epithelia in other parts of the eye that separate the intraocular contents from the blood, such as the iris blood vessels or ciliary body epithelium.

The main clinical tool currently available for studying the functional integrity of the blood ocular barriers is the dye fluorescein. Fluorescein has the chemical property of glowing bright green when illuminated with a blue light. Therefore, fluorescein can be injected into a vein in the arm; and as the fluorescein circulates it can be seen to flow through the blood vessels of the eye. Using appropriate blue illumination, the blood vessels of the eye can be visualized with high contrast as the fluorescein flows through them. This clinical test is called fluorescein angiography. This technique has been used to study retinal diseases and has recently been applied in an attempt to study diseases of the front part of the eye as well.

It is an essential property of the normal retinal blood vessels and the epithelium underneath the retina that they impede the diffusion of fluorescein into the eye. In short, fluorescein illustrates some properties of the blood-retinal barrier. In certain disease states, however, permeability may be altered; fluorescein leaks from the blood vessels of the retina or through the epithelium of the retina. The existence of such leakage is important diagnostically and therapeutically.

Fluorescein has a long history of use in medicine but the prime reasons it has been applied to ophthalmology are that it is, (a) safe and (b) easily visualized. During the past twenty years fluorescein angiography has developed into a powerful tool to study the blood-ocular barriers.

The question of fluorescein permeability, however, is a complex one.

Anatomical disruption of these epithelial and vascular structures leads to abnormal fluorescein leakage. For instance, recently, with the application of vitreous fluorophotometry, it has been noted that fluorescein accumulation within the eye may occur in the absence of a specific anatomical defect. Instead, fluorescein penetration can result from functional alterations of the barrier cells.

There are four main characteristics of a chemical that determine whether it will pass across the blood-ocular barriers. First, molecular size is important; smaller molecules cross more readily. Second, the tendency of a chemical to bind to plasma proteins affects passage. Third, substances with high lipid solubility pass more easily than those with a low lipid solubility. Fourth, there are transport mechanisms at the cellular level for moving metabolites or nutrients one way or the other across these barriers; a chemical structurally related to a naturally occurring chemical may move by such a transport mechanism.

The physical properties of the fluorescein molecule and the nature of its interactions with the barrier cells complicate the interpretation of dye leakage. By virtue of size, that portion of intravascular fluorescein bound to plasma proteins or absorbed to red blood cells does not cross the blood-ocular barriers. In contrast unbound dye can diffuse to some extent through the plasma membranes of barrier cells. The tendency of fluorescein or any organic electrolyte to penetrate cell membranes is related to its partition coefficient which reflects lipid solubility, to its dissociation coefficient ($K_a$); to its molecular weight, and to pH (3-5). Fluorescein, equilibrated between octanol and artificial sea water, has a partition coefficient of 0.6 indicating considerable dye solubility in the non-polar phase, and by inference considerable permeability in cell membranes. This relatively high partition coefficient is consistent with the observation that the half-time of fluorescein leakage from liposomes is only 5 minutes. Further, the $pK_a$ of the equilibrium between the divalent and monovalent forms of the fluorescein anion is 6.7, a value not far removed from physiological pH. Although most of the dye is in the divalent form at this pH, a significant amount of the less polar monoanion is also present. Small pH changes in the physiological range, by altering the relative concentrations of the two ionic species, can be expected to change the membrane penetration.

Passive diffusion is not the only factor affecting transfer of unbound fluorescein across the blood-ocular barriers. The dye also serves as a substrate for an active transport system in the anterior uvea and probably in the posterior segment as well. In both regions the direction of transport appears to be outward, that is, from eye to blood. This active process presumably opposes inward diffusion of fluorescein through barrier cell membranes, minimizing net transfer of dye from blood to intraocular structures in normal eyes.

Fluorescein is handled by these mechanisms. Therefore, from the foregoing, it can be seen that the question of fluorescein permeability at the blood-ocular barriers and the true meaning of fluorescein "leakage" is indeed complex. As an indicator of barrier function fluorescein has a major drawback. It has a high lipid solubility at blood pH.

Carboxyfluorescein has now been determined to overcome this shortcoming of fluorescein. Carboxyfluorescein differs from fluorescein by the addition of a carboxyl group to the basic fluorescein molecule. As a result, carboxyfluorescein is much more water soluble and much less lipid soluble than fluorescein. The factor here is approximately 1,000. This makes carboxyfluorescein considerably less likely to cross the blood retinal barrier by solubility. The ability of carboxyfluorescein to pass the blood ocular barriers by specific cellular transport mechanisms seems to parallel fluorescein. The molecular size of fluorescein and carboxyfluorescein is about the same. Finally, the fluorescent properties of fluorescein, both wavelength and quantum efficiency are also present to an equal degree in carboxyfluorescein, so that both dyes can be visualized as easily in the eye.

Thus, carboxyfluorescein is a dye with better solubility properties than fluorescein in the definition of barrier integrity while being similar both in visibility and transport quality. Since lipid solubility is the biggest drawback to fluorescein, carboxyfluorescein has now been determined to be a worthwhile replacement in ophthalmic diagnosis.

Carboxyfluorescein has the following structural formula:

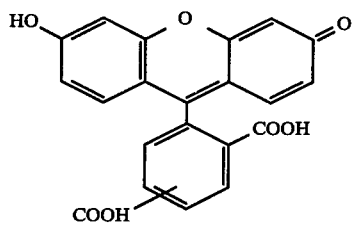

Carboxyfluorescein as sold commercially (Kodak) is a mixture of 4 carboxyfluorescein and 5 carboxyfluorescein isomers. Either or both of these are active (active isomer) and it is conceivable that other isomers are active. Some commercial literature apparently incorrectly names the compound as 5 (6) carboxyfluorescein or 6-carboxyfluorescein, but in any event the present invention involves only active isomers of carboxyfluorescein.

Prior uses for carboxyfluorescein include a technique wherein carboxyfluorescein is incorporated into small lipid vesicles (lipsomes) and the interaction of these lipsomes with cells in culture is studied. Another prior use involves performing microinjections of carboxyfluorescein into individual cells in culture and studying the movement of this dye across open cell junctions. Both of these applications involve the use of cells in tissue culture and do not contemplate the potential application and development of carboxyfluorescein as a dye for clinical diagnosis.

To determine whether a less membrane permeable dye than fluorescein has value as a probe of the structural and functional integrity of the blood-ocular barriers we have undertaken studies of carboxyfluorescein, a compound with the same fluorescence characteristics as fluorescein, but with lower lipid solubility at physiological pH (7). In particular, the lipid solubility of carboxyfluorescein was compared with fluorescein by measuring dye partitioning between octanol and aqueous buffer at different pH to determine solubility behavior relevant to the permeability of cell membranes in vivo. Studies were then made of the ocular distribution carboxyfluorescein in rats after intravenous injection using quantitative fluorescence microscopy; and compared to the results for fluorescein. The plasma binding of carboxyfluorescein was also studied and compared to fluorescein.

Octanol/buffer partition ratios: The ratio of concentrations of a given solute in equilibrium distribution between two immiscible solvents is termed the partition coefficient. This expression properly refers only to the distribution of a single molecular species between the two phases. Both solutes studied exist as a mixture of ionized forms within the pH range tested. Total dye concentration in the two solvent phases was measured without correction for ionization or self-association and the recommended term, "partition ratio", is used to refer to these uncorrected distributions.

Carboxyfluorescein (Eastman Kodak Co., Rochester) or sodium fluorescein (Sigma Chemical Co., St. Louis) was dissolved at concentrations of $10^{-3}$ M or $10^{-5}$ M in octanol-saturated 0.1 M phosphate buffer at different pH values between 6.40 and 8.03. The aqueous dye solutions were equilibrated with equal volumes of buffer-saturated octanol by 100 inversions during 5 minutes, and the phases were separated by centrifugation. Dye concentrations were measured spectrofluorophotometrically at excitation and emmision wavelengths of 487 and 512 nm, respectively, with an Aminco-Bowman Ratio Spectrofluorophotometer.

Two methods were used to calculate partition ratios. In the first, the dye concentration in the aqueous phase was measured before ($C_b$) and after ($C_a$) partitioning, and the ratio was obtained from the equation:

$$P.R. = C_{oct}/C_{aq} = (C_b - C_a)/C_a,$$

where $C_{oct}$ and $C_{aq}$ are the dye concentration in the octanol and aqueous phases respectively after equilibration. In the second method, concentration in the octanol phase was determined by extracting the dye from octanol with an equal volume 0.1 N NaOH. Concentration in the octanol phase could not be measured directly because of the marked loss of fluorescence of both dyes in this solvent. A single base extraction of the octanol recovered 99% of the dissolved fluorescein and 99.9% of the dissolved carboxyfluorescein. Therefore, dye concentration in the first base extract was accepted as the concentration in the octanol phase and calculated the partition ratio from the equation:

$$P.R. = C_{oct}/(C_b - C_{oct})$$

Both methods for determining the partition ratio gave similar results when more than 10% of the initial dye concentration was removed from the aqueous phase by partitioning. When very small quantities of dye were removed, measurement of concentration differences in the aqueous phase before and after partitioning became unreliable, and we used only the second method to calculate the ratio.

Intra-ocular dye distribution: Young male Wistar rats (180–250 g) under pentobarital anesthesia (50 mg/kg i.p.) were injected intravenously with carboxyfluorescein or fluorescein solutions (pH 7.4) at doses of 12.5, 62.5 and 125 mg/kg. One minute after dye injection, the eyes were removed and immediately frozen in isopentane cooled to −110° C. by a liquid nitrogen bath. Between 2 and 4 minutes after injection a blood sample from the abdominal aorta was drawn into a heparinized syringe for determination of the concentration of unbound dye in plasma. The frozen eyes were dried under vacuum at −35° C. and embedded in paraffin. After embedding the eyes were stored under vacuum at −20° C. to minimize the development of autofluorescence. Additional eyes from normal rats not injected with dye were processed and stored identically for measurement of tissue autofluorescence. Immediately prior to examination with the fluorescence microscope, sections were cut at a thickness of 12 microns, placed on glass slides, and mounted with xylene.

Fluorescence intensity in small areas of the tissue sections was measured with a 450 u fiber optic probe placed in the object plane of an ocular and connected to a photomultiplier tube. An amplified signal from the photomultiplier was recorded with a digital voltmeter. The illumination system consisted of a 50 W high pressure mercury light source and an epifluorescence condensor equipped with a 455–490 nm exciter filter, a 510 nm dichroic beam splitter, and a 520 nm barrier filter. All measurements were performed using a 63X oil objective (N.A. 1.4). With this magnification, an aperture in the object plane restricted the area of illumination to a circle, 24 microns in diameter. The fiber optic probe covered a specimen field, 6 microns in diameter, centered in the larger illuminated field.

Fluorescence intensity of four tissue layers was recorded in the posterior segment: the inner plexiform, outer nuclear, and photoreceptor outer segment layers of the retina, and the choriocapillaris. Each of these layers is of sufficient width so that the illuminated area encompassed a homogeneous field. Foci of intense fluorescence, such as dye filled retinal capillaries, within the illumination field but outside the detection area of the fiber optic probe, can increase the recorded signal by light scatter into the detection area. Fields containing such bright foci were avoided. Examination of the section, location of the area for measurement, and focusing of the image was accomplished under dim green illumination from a tungsten lamp. The illumination was then switched to the fluorescence system, and the maximum value of fluorescence intensity was recorded as voltage. Measurements were made at 12 sites in each layer to obtain the average fluorescence intensities for an individual eye. These values were then corrected for tissue autofluorescence by subtracting the average fluorescence intensity of each layer in eyes from animals not injected with dye.

The response characteristics of the recording system are such that in the time required to reach a peak reading, significant fading occurs; the recorded value, therefore, does not represent the maximum fluorescence intensity of the tissue. It was established, however, that the peak reading is linearly proportional to dye concentration in solution, and we assume that it is similarly proportional to dye concentration in tissue sections. The measurements obtained represent relative fluorescence intensity only, and not absolute dye concentration in tissue.

Measurement of unbound dye in plasma: Plasma was separated by centrifugation from the heparinized blood obtained from rats injected with sodium fluorescein or carboxyfluorescein in the intraocular dye distribution study. The plasma was dialyzed for 24 hours at 37° C. against 0.1 M phosphate buffer at pH 7.4 using cellulose dialysis tubing with a 3500 molecular weight cut-off. Dye concentration was measured in the dialysate spectrofluorophotometrically and from this value calculated the unbound plasma dye concentration.

To study the fraction of unbound dye in human plasma, there was added small aliquots of carboxyfluorescein and sodium fluorescein solutions to plasma separated from heparinized human blood so that the final dye concentration in the plasma was between $10^{-3}$ M and $10^{-6}$ M. The plasma/dye mixture was incubated for 2 hours at 37° C. Then using the dialysis and measuring procedures described above, the ratio of unbound dye to total dye in the plasma mixture was calculated.

RESULTS

Partition ratios: the measured octanol/buffer partition ratios (Table I) demonstrate that, over the pH range tested, carboxyfluorescein is approximately 1000 times less soluble than fluorescein in the octanol phase. A hundred-fold change in dye concentration has no effect on the equilibrium distribution.

TABLE I
PARTITION RATIOS OF CARBOXYFLUORESCEIN AND FLUORESCEIN AT DIFFERENT pH

| DYE CONCENTRATION | pH | | | |
|---|---|---|---|---|
| | 6.42 | 6.87 | 7.38 | 8.03 |
| CARBOXY FLUORESCEIN | | | | |
| $10^{-3}$M | .033 | .0028 | .0008 | .00006 |
| $10^{-5}$M | .037 | .0030 | .0007 | — |
| FLUORESCEIN | | | | |
| $10^{-3}$M | 35 | 5.1 | .51 | .038 |
| $10^{-5}$M | 38 | 4.9 | .64 | .030 |

Variation of pH, however, profoundly laters the partition ratios; as pH falls, octanol solubility of both dyes increases. When the logarithm of the partition ratio is plotted against pH, linear relationships of similar slope are demonstrated for both carboxyfluorescein and fluorescein. Despite the exponential increase of partition ratios with decreasing pH, the ratios for carboxyfluorescein remain well below 0.1 even at pH 6.4, the lowest value tested. Fluorescein, on the other hand, reaches a partition ratio of 1.0 at pH 7.25, not far removed from normal plasma pH.

INTRAVENOUS USE OF CARBOXY FLUORESCEIN

Intraocular dye distribution: the histological localization of fluorescence in sections from eyes of rats injected with carboxyfluorescein differs markedly from that found with fluorescein. At one minute after injection of either dye, brilliant fluorescence is seen within all blood vessels and throughout the stroma of the choroid and ciliary processes. In the anterior segment, however, cells of the ciliary epithelium which are brightly stained by fluorescein, show no detectable fluorescence with carboxyfluorescein though the adjacent intercellular spaces open to the stroma are well-filled by the dye. The iris stroma contains some carboxyfluorescein, but the intensity of fluorescence is less than that seen with fluorescein; the iris epithelium, like the ciliary epithelium remains dark in these short-term experiments. In the posterior segment, no fluorescence is seen in retinal tissue following carboxyfluorescein injection, whereas, in comparison, a diffuse dim fluorescence is seen in all layers of the retina in animals given fluorescein.

Quantitative measurements of fluorescence intensity in the retina extend the impressions gained from visual inspection (Table II) herein below. Animals injected with carboxyfluorescein have concentrations of unbound dye in plasma which are significantly higher than in animals injected with fluorescein. However, despite high fluorescence intensity levels measured in the choroid, there is virtually no detectable fluorescence in retinal tissue. The negligible values that are recorded in the retinal layers could indicate a very low tissue concentration of carboxyfluorescein, more likely, they are an artifact caused by light scattered from flecks of dye displaced along the surface of the tissue section from cut blood vessels.

TABLE II

| | | TISSUE RELATIVE FLUORESCENCE INTENSITY (MEAN ± S.E.M.)* | | | | |
|---|---|---|---|---|---|---|
| DOSE (MG/KG) | PLASMA UNBOUND DYE CONCENTRATION (MG/ML) | CHOROID | OUTER SEGMENTS | ONL | IPL | n |
| CARBOXYFLUORESCEIN | | | | | | |
| 125 | .55 ± .03 | 7.8 ± .8 | .006 ± .003 | .003 ± .001 | .002 ± .001 | 4 |
| 62.5 | .29 ± .01 | 8.0 ± .4 | .008 ± .001 | .002 ± .001 | .001 ± .001 | 5 |
| FLUORESCEIN | | | | | | |
| 125 | .29 ± .01 | 5.7 ± .5 | .452 ± .021 | .196 ± .011 | .150 ± .034 | 6 |
| 62.5 | .18 ± .01 | 2.7 ± .2 | .153 ± .008 | .076 ± .004 | .086 ± .008 | 6 |
| 12.5 | .04 ± .03 | .57 ± .03 | .032 ± .003 | .011 ± .001 | .021 ± .002 | 6 |

*Corrected for tissue autofluorescence as described in the text.

In contrast to carboxyfluorescein, significant fluorescence intensity is measured in the retinas of all animals injected with fluorescein. Importantly, the fluorescein levels of choriocapillaris and the retinal layers are proportional to the administered dose. Values recorded in the outer segment layer are 6–8% of those measured in the choroid, and are, in turn, twice as high as those of the deeper retinal layers. Although fluorescence intensity to dye concentration cannot be precisely related, the high levels recorded at the photoreceptor outer segment layer indicate a concentration gradient across the retina, and suggest that much of the dye enters the retina by way of the pigment epithelium.

Though the measurements of plasma unbound dye concentration in rats (Table II) precludes extensive plasma binding as the cause of the very low ocular penetration of carboxyfluorescein, the binding of the two dyes in plasma obtained from human blood (Table III) hereinbelow was further related. Large amounts of free carboxyfluorescein and free fluorescein are present over the entire dye concentration range tested, and carboxyfluorescein is consistently less bound to human plasma proteins than fluorescein.

TABLE III

DIALYZABLE FRACTION OF CARBOXYFLUORESCEIN AND FLUORESCEIN IN HUMAN PLASMA

| | DIALYZABLE FRACTION (N) MEAN ± S.E.M. | |
|---|---|---|
| PLASMA CONCENTRATION | CARBOXY-FLUORESCEIN | FLUORESCEIN |
| $10^{-3}$M | (4) .61 ± .02 | (4) .30 ± .02 |
| $10^{-4}$M | (4) .50 ± .01 | (2) .33 ± .03 |
| $10^{-5}$M | (6) .51 ± .03 | (4) .33 ± .01 |
| $10^{-6}$M | (2) .46 ± .01 | (2) .32 ± .02 |

The blood-ocular barriers are markedly less permeable to intravascular carboxyfluorescein than to fluorescein. The relative inability of carboxyfluorescein to cross these barriers is not caused by more extensive binding to plasma proteins; rather, the lower lipid solubility of carboxyfluorescein significantly reduces penetration through barrier cell membranes.

Octanol/buffer partition ratios, used to estimate lipid solubility are 1000 times lower for carboxyfluorescein than for fluorescein, and ratios for both dyes are very sensitive to pH changes. Precise description of the partitioning behavior of such charged molecules is complicated not only by pH effects, but also by possible solute association and variable hydration in different phases. The partition ratio does not fully characterize the distribution of these two dyes, but the magnitude of the difference between the partition ratios for carboxyfluorescein and fluorescein is not only a valid reflection of the relative lipid solubilities, it also presages the compartive tissue distribution of the two dyes.

The partition ratios for fluorescein are of particular interest because of their high values in the physiological pH range. In studying the partitioning of fluorescein between octanol and artificial sea water, a distribution ratio of 0.6, was found very close to what we measured at pH 7.38. In aqueous solution, fluorescein can exist in four forms; the dianion, monoanion, neutral molecule, and the cation, with respective $pK_a$ values of 6.7, 4.4, and 2.2. The dianion and monoanion forms predominate within the pH range of 6.4 to 8.0, and the marked increase of partition ratio with decreasing pH in this interval indicates that the monoanion is very much more lipid soluble than the dianion. However, the rate of increase of the partition ratio is greater than would be expected simply from an increase in concentration of the monoanion as estimated from $pK_a$ and pH. This discrepancy suggests that other undetermined factors increase dye transfer to the non-polar phase. Ionization constants for carboxyfluorescein are not available to our knowledge, but, on the basis of partition ratios, the additional carboxyl substituent probably has a $pK_a$ low enough to provide increased molecular polarity throughout the pH range studied. The presence of another ionized carboxyl group also may explain the reduced binding of carboxyfluorescein to plasma protein in view of the hydrophobic nature of the fluorescein binding site on albumin.

Intraocular dye distribution at one minute after intravenous dye injection reflects well the difference in lipid solubility of carboxyfluorescein and fluorescein. Very little carboxyfluorescein penetrates the barrier layers of the anterior and posterior segments. Thus, it cannot be seen within the cells of the ciliary epithelium and ir is epithelium, nor in retinal tissue. In contrast, fluorescein brightly stains the cells of the ciliary and iris epithelium, and can be seen to a lesser extent in all retinal layers.

Quantitative measurements of fluorescence intensity in the choroid and retina confirmed that, in comparison to fluorescein, (even when very high doses of dye are given) carboxyfluorescein enters retinal tissue, or in negligible amounts. Much greater amounts of fluorescein, on the other hand, were detected throughout the retina with fluorescence intensity levels proportional to the dose administered. The highest fluorescein readings in the retina were recorded in the outer segment layer suggesting significant penetration across the pigment epithelium. Some diffusion of fluorescein should also occur through the walls of retinal vessels.

It is believed that carboxyfluorescein has potential for experimental and clinical use as a probe of the blood-ocular barrier. It is similar to fluorescein in molecular weight, in spectral properties, including quantum efficiency, and, like fluorescein, a significant proportion of carboxyfluorescein is not bound to plasma proteins. The lower lipid solubility of carboxyfluorescein, however, significantly reduces diffusion across barrier membranes. This property may yield better definition of the nature of barrier abnormalities than is now possible with fluorescein.

TOPICAL USE OF CARBOXYFLUORESCEIN

Carboxyfluorescein was prepared as a 1% solution in water, buffered to pH 7.4. Carboxyfluorescein was made into strip form, using strips of #1 filter paper, impregnated with carboxyfluorescein and allowed to dry. The carboxyfluorescein was applied to rabbit eyes both with the paper impregnated strip and also as a 1% topical drop. The topical application of carboxyfluorescein caused no apparent hyperemia or corneal changes within 5 to 10 minutes of application. In addition, when applied to an awake rabbit, the rabbit did not react in a negative fashion, thus suggesting no subjective discomfort associated with the application of carboxyfluorescein.

When applied topically to rabbit eyes, carboxyfluorescein is seen in the tear film and has its characteristic green fluorescence when illuminated by a blue light. An experimentally produced corneal abrasion, was made on the eye of a rabbit under general anaesthesia, and carboxyfluorescein densely stained the corneal epithelial defect. The stain persisted but lessened in intensity during an observation period of 30 to 45 minutes. When the aqueous humor from the anterior chamber of the eye is removed approximately 45 minutes after the corneal abrasion and the application of carboxyfluorescein, with the rabbit under general anesthesia, the aqueous humor is seen to contain the dim green fluorescence of carboxyfluorescein when examined under a blue light. In the control eye where the corneal epithelium was not removed experimentally, markedly less carboxyfluorescein was seen in the aqueous humor of the eye.

These observations with carboxyfluorescein are entirely similar to observations made clinically in humans with fluorescein, the dye currently used topically to visualize the tear film and to outline defects in the corneal epithelium. It is believed that penetration of the cornea by carboxyfluorescein would be less than the penetration of the cornea by fluorescein. One of the major disadvantages of topical fluorescein is that its ready penetration through the cornea into the aqueous humor creates an artificial aqueous flare, commonly called "fluorescein flare." This flare can be confused with a condition seen in ocular inflammation and on occasion can lead to some difficulties in diagnosis. The lower lipid solubility, and presumably lower penetration of carboxyfluorescein through the cornea, would reduce this problem. For this reason, it is believed that carboxyfluorescein is not only an adequate substitute for fluorescein in topical use, but may indeed prove to have a substantial advantage over fluorescein.

The current topical uses of fluorescein include: (1) visualization of the tear film (in diagnosing dry eyes, fitting contact lenses, studying lacrimal duct function, recording intraocular pressure in humans by the technique of applanation tonometry, etc.); (2) staining of abnormalities of the outer layer of the cornea called the corneal epithelium, (as in diagnosing corneal abrasions, assessing various infections or other disorders of the superficial cornea, etc.); (3) assessing ocular integrity after surgery or penetrating injuries (Seidel test); (4) use as a market for aqueous humor dynamics (a research application in which fluorescein is applied to the cornea and aided in its pentration into the aqueous humor by the application of a very weak electrical current after which the disappearance of fluorescein from the eye is used to study the flow rates of aqueous humor); and (5) as a method of studying corneal permeability. The invention contemplates the use of carboxyfluorescein for all these purposes.

Without further elaboration the foregoing will so fully illustrate our invention that others may, by applying current or future knowledge, readily adapt the same for use under various conditions of service.

What is claimed as the invention is:

1. The method of performing ophthalmic studies comprising applying to the eye an effective amount therefor of at least one active isomer of carboxyfluorescein.

2. The method of claim 1 wherein said carboxyfluorescein is administered intraveneously.

3. The method of claim 1 wherein said carboxyfluorescein is administered topically.

* * * * *